US008703449B2

(12) United States Patent
Martin et al.

(10) Patent No.: US 8,703,449 B2
(45) Date of Patent: *Apr. 22, 2014

(54) BIOABSORBABLE POLYMER CONTAINING 2-HYDROXYACID MONOMERS

(75) Inventors: David P. Martin, Arlington, MA (US); Frank A. Skraly, Watertown, MA (US)

(73) Assignee: Metabolix, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/250,492

(22) Filed: Sep. 30, 2011

(65) Prior Publication Data

US 2012/0021471 A1    Jan. 26, 2012

Related U.S. Application Data

(63) Continuation of application No. 10/434,334, filed on May 7, 2003, now Pat. No. 8,039,237.

(60) Provisional application No. 60/379,583, filed on May 10, 2002.

(51) Int. Cl.
| | |
|---|---|
| *C12P 7/62* | (2006.01) |
| *C12N 1/20* | (2006.01) |
| *C12N 15/00* | (2006.01) |
| *C12Q 1/00* | (2006.01) |
| *C12N 9/04* | (2006.01) |
| *C12N 9/10* | (2006.01) |
| *C12N 9/02* | (2006.01) |
| *C07H 21/04* | (2006.01) |

(52) U.S. Cl.
USPC ............... 435/135; 435/252.3; 435/320.1; 435/4; 435/190; 435/193; 435/189; 536/23.2

(58) Field of Classification Search
None
See application file for complete search history.

(56) References Cited

U.S. PATENT DOCUMENTS

| | | | |
|---|---|---|---|
| 3,736,646 | A | 6/1973 | Schmitt |
| 3,867,190 | A | 2/1975 | Schmitt |
| 4,910,145 | A | 3/1990 | Holmes |
| 5,245,023 | A | 9/1993 | Peoples |
| 5,250,430 | A | 10/1993 | Peoples |
| 5,480,794 | A | 1/1996 | Peoples |
| 5,489,470 | A | 2/1996 | Noda |
| 5,512,669 | A | 4/1996 | Peoples |
| 5,520,116 | A | 5/1996 | Toyre |
| 5,534,432 | A | 7/1996 | Peoples |
| 5,563,239 | A | 10/1996 | Hubbs |
| 5,973,100 | A | 10/1999 | Asrar |
| 6,329,183 | B1 | 12/2001 | Skraly |
| 6,548,569 | B1 | 4/2003 | Williams |
| 6,576,450 | B2 | 6/2003 | Skraly |
| 6,610,764 | B1 | 8/2003 | Martin |
| 2002/0164729 | A1 | 11/2002 | Skraly |
| 2003/0017576 | A1 | 1/2003 | Aquin |
| 2004/0023347 | A1 | 2/2004 | Skraly |
| 2005/0239179 | A1 | 10/2005 | Skraly |

FOREIGN PATENT DOCUMENTS

| | | |
|---|---|---|
| WO | 9805182 | 11/1998 |
| WO | 9932536 | 7/1999 |
| WO | 0008198 | 2/2000 |
| WO | 0056376 | 9/2000 |
| WO | 0208428 | 1/2002 |
| WO | 0240690 | 5/2002 |

OTHER PUBLICATIONS

Agostini, et al., "Synthesis and Characterization of Poly-β-Hydroxybutyrate. I. Synthesis of Crystalline DL Poly-β-Hydroxybutyrate from DL-β-Butyrolactone," Polym. Sci. Part A 19:2775 87 (1971).
Anderson, et al., "Occurrence, metabolism, metabolic role and industrial uses of bacterial polyhydroxyalkanoates", Microbiol. Rev., 54(4):450-72 (1990).
Braunegg, et al., "Polyhydroxyalkanoates, biopolyesters from renewable resources: physiological and engineering aspects," J. Biotech. 65: 127-161 (1998).
Bruhn & Müller, "Preparation and characterization of spray-dried poly(DL-lactide) Micro Spheres," Proceed. Intern. Symp. Control. Rel. Bioact. Mater. 18:668-69 (1991).
Byrom, "Miscellaneous Biomaterials" in Biomaterials (D. Byrom, ed.) pp. 333 59 (MacMillan Publishers, London 1991).
Cao, et al., "Thermal and morphological study of fractionated poly(3-hydroxybutyric acid-co-3-hydroxypropionic acid)," Macromol. Chem. Phys. 198: 3539-3557 (1997).
Choi & Lee, "Factors affecting the economics of polyhydroxyalkanoate production by bacterial fermentation," Appl. Microbiol. Biotechnol. 51: 13-21 (1999).
Chujo, et al., "Ring-opening polymerization of glycolide," Die Makromol. Chem. 100: 262-266 (1967).
Conti, et al., "Use of polylactic acid for the preparation of microparticulate drug delivery systems," J. Microencapsulation 9: 153-166 (1992).
Doi, "Microbial synthesis, physical properties, and bioegradability of polyhydroxyalkanoates," Macromol. Symp. 98: 585-599 (1995).
Dubois, et al., "Macromolecular engineering of polylactones and polylactides. 12. Study of the depolymerization reactions of pol( -caprolactone) with functional aluminum alkoxide end groups," Macromolecules 26:4407-4412 (1993).
Fukuzaki, et al., "A new biodegradable copolymer of glycolic acid and lactones with relatively low-molecular weight prepared by direct copolycondensation in the absence of catalysts," J. Biomed. Mater. Res. 25(3): 315-328 (1991).

(Continued)

*Primary Examiner* — Yong Pak
(74) *Attorney, Agent, or Firm* — Pabst Patent Group LLP (57) ABSTRACT

Genetically engineered organisms for production of PHA copolymers containing 2-hydroxyacid monomers and the methods of making and using thereof have been developed. The copolymers containing 2-hydroxyacid monomers can be synthesized via biosynthesis by the action of a PHA polymerase in a living cell. By changing the genetic background of the cells, one can control specific metabolic pathways allowing control of the level of glycolic acid co-monomer in the PHA polymer.

11 Claims, 2 Drawing Sheets

(56) References Cited

OTHER PUBLICATIONS

Fukuzaki, et al., "Direct copolymerization of glycolic acid with lactones in the absence of catalysts," Eur. Polym. J. 26(4): 457-61 (1990).
Gerngross & Martin, "Enzyme-catalyzed synthesis of poly[(R)-(-)-3-hydroxybutyrate]: formation of macroscopic granules in vitro," Proc. Natl. Acad. Sci. USA 92:6279-83 (1995).
Gross, et al., "Polymerization of β-monosubstituted-β-propiolactones using trialkylaluminum-water catalytic systems and polymer characterization," Macromolecules 21:2657-68 (1988).
Hein, et al., "Biosynthesis of poly(4-hydroxybutyric acid) by recombinant strains of *Escherichia coli*," FEMS Microbiol. Lett. 153: 411-418 (1997).
Herrero, et al "Transposon vectors containing non-antibiotic resistance selection markers for cloning and stable chromosomal insertion of foreign genes in gram-negative bacteria," J. Bacteriol. 172(11): 6557-6567 (1990).
Hocking & Marchessault, "Syndiotactic poly[(R,S)-β-hydroxybutyrate] isolated from methyaluminoxane-catalyzed polymerization," Polym. Bull. 30:163-70 (1993).
Hocking & Marchessault, "Biopolyesters" in Chemistry and Technology of Biodegradable Polymers, (G.J.L. Griffin, ed.), pp. 48-96, Chapman and Hall: London, 1994.
Holmes, "Biologically Produced (R)-3-Hydroxyalkanoate Polymers and Copolymers," in Developments in Crystalline Polymers (Bassett, ed.) Elsevier: London, pp. 1-65 (1988).
Hori, et al., "Ring-opening copolymerization of optically active β-butyrolactone with several lactones catalyzed by distannoxane complexes: synthesis of new biodegradable polyesters," Macromolecules 26:4388-90 (1993).
Hori, et al., "Ring-opening polymerization of optically active β-butyrolactone using distannoxane catalysts: synthesis of high molecular weight poly(3-hydroxybutyrate)," Macromolecules 26:5533-34 (1993).
Jesudason & Marchessualt, "Synthetic poly[(R,S)—hydroxyalkanoates] with butyl and hexyl side chains," Macromolecules 27: 2595-2602 (1994).
Johnson & Lin, "*Klebsiella pneumoniae* 1,3-propanediol: NAD+ oxidoreductase," J. Bacteriol. 169(5): 2050-2054 (1987).
Kemnitzer, et al., "Preparation of predominantly syndiotactic poly(β-hydroxybutyrate) by the tributylin methoxide catalyzed ring-opening polymerization of racemicil β-butyrolactone," Macromolecules 26:1221 29 (1993).
Khelifa, et al., "Synthesis of 2-hydroxyacid from 2-amino acid by *Clostridium butyricum*", Bioorganic & Medicinal Chem. Left., 8(23):3429-3434 (1998).
Koosha, "Preparation and characterization of biodegradable polymeric drug carriers," Ph.D. Dissertation, 1989, Univ. Nottingham, UK., Diss. Abstr. Int. B 51:1206 (1990).
Kricheldorf, "Polylactones, 2. Copolymerization of glycolide with—propiolactone, -butyrolactone or -valerolactone," Makromol. Chem. 186(5): 955-976 (1985).
Lafferty, et al., "Microbial Production of Poly-b-hydroxybutyric acid" in Biotechnology (H.J. Rehm and G. Reed, eds.), Verlagsgesellschaft, Weinheim, vol. 66, pp. 135-176 (1988).
Le Borgne & Spassky, "Stereoelective polymerization of β-butyrolactone," Polymer 30:2312 19 (1989).
Madison & Huisman, "Metabolic engineering of poly(3-hydroxyalkanoates): from DNA to plastic," Microbiol. Mol. Biol. Rev. 63(1): 21-53 (1999).
Mathiowitz & Langer, "Polyanhydride microspheres as drug delivery systems" in Microcapsules Nanopart. Med. Pharm. (Donbrow, ed.) CRC Press: Boca Raton, Florida, pp. 99 123 (1992).
Maysinger, et al., "Microencapsulation and the grafting of genetically transformed cells as therapeutic strategies to rescue degenerating neurons of the CNS," Rev. Neurosci., 6:1533 (1995).
McMillin, et al., "Elastomers for biomedical applications," Rubber Chemistry and Technology 67:417-446 (1994).
Miller, Experiments in Molecular Genetics, Cold Spring Harbor Laboratory Press: Cold Spring Harbor, NY (1972).
Müller & Seebach. "Poly(hydroxyalkanoates): a fifth class of physiologically important organic biopolymers," Angew. Chem. Int. Ed. Engl. 32: 477 502 (1993).
Nakayama, et al., "Syntheses of biodegradable polyesters and effect of chemical structure on biodegradation," Nippon Kagaku Kaishi 1: 1-9 (2001).
Nakayama, et al. "Synthesis and biodegradability of novel copolyesters containing -butyrolactone units," Polymer 39(5): 1213-1222 (1998).
Nunez, et al., Biochemical characterization of the 2-ketoacid reductases encoded by ycdW and yiaE genes in *Escherichia coli*, Biochem. J., 354(3):707-15 (2001).
Ogawa, et al., "A new technique to efficiently entrap leuprolide acetate into microcapsules of poly lactic acid or copoly(lactic/glycolic) acid," Chem. Pharm. Bull. 36:1095-103 (1988).
Saito, et al., "Microbial synthesis and properties of poly(3-hydroxybutyrate-co-4-hydroxybutyrate)," Polym. Int. 39: 169 (1996).
Sambrook, et al Molecular cloning: A Laboratory Manual, 2nd ed., Cold Spring Harbor Laboratory Press, Cold Spring Harbor, NY, 1989).
Shimamura, et. al., "Microbial synthesis and characterization of poly(3-hydroxybutyrate-co-3-hydroxypropionate)," Macromolecules 27: 4429-4435 (1994).
Skraly, et al, "Construction and characterization of a 1,3-propanediol operon," Appl. Environ. Microbiol. 64: 98-105 (1998).
Skraly, "Polyhydroxyalkanoates produced by recombinant *E. coli*" , poster at Engineering Foundation Conference: Metabolic engineering (1998).
Söhling & Gottschalk, "Molecular analysis of the anaerobic succinate degradation pathway in *Clostridium kluyveri*," J. Bacteriol. 178:871-880 (1996).
Sophos, et al., "Aldehyde dehydrogenase gene superfamily" , Chem. Biol. Interact., 130-132 (1-3):323-37 (2001).
Steinbüchel & Valentin, "Diversity of bacterial polyhydroxyalkanoic acids," FEMS Microbiol. Lett. 128:219-28 (1995).
Steinbüchel & Wiese, "A *Pseudomonas* strain accumulating polyesters of 3-hydroxybutyric acid and medium-chain-length 3-hydroxyalkanoic acids," Appl. Microbiol. Biotechnol. 37:691-97 (1992).
Steinbüchel, "Polyhydroxyalkanoic Acids" in Biomaterials (Byrom, ed.) MacMillan Publishers: London, pp. 123 213 (1991).
Sudesh, et al., "Synthesis, structure and properties of polyhydroxyalkanoates: biological polyesters", Prog. Polym. Sci., 25(10):1503-55 (2000).
Tanahashi & Doi, "Thermal properties and stereoregularity of poly(3-hydroxybutyrate) prepared from optically active β-butyrolactone with a zinc-based catalyst," Macromolecules 24:5732-33 (1991).
Tsuage, et al., "Molecular cloning of two ®-specific enoyl-CoA hydratase genes from *Pseudomonas aeruginosa* and their use for polyhydroxyalkanoate synthesis" , FEMS Microbiol. Lett., 184(2):193-98 (2000).
Valentin, et al., "Identification of 4-hydroxyhexanoic acid as a new constituent of biosynthetic polyhydroxyalkanoic acids from bacteria," Appl. Microbiol. Biotechnol. 40:710-16 (1994).
Valentin, et al., "Application of a Propionyl Coenzyme A Synthetase for Poly (3-hydroxypropionate-co-3-Hydroxybutyrate) Accumulation in Recombinant *Escherichia coli*," Appl. Environ. Microbiol. 66(12): 5253-5258 (2000).
Valentin, et al., "Identification of 4-hydroxyvaleric acid as a constituent of biosynthetic polyhydroxyalkanoic acids from bacteria," Appl. Microbiol. Biotechnol. 36: 507-514 (1992).
Van Beilen, et al., "DNA sequence determination and functional characterization of the OCT-plasmid-encoded alkJKL genes of *Pseudomonas oleovorans*," Mol. Microbiol. 6(21): 3121-3136 (1992).
Williams, et al., "PHA applications: addressing the price performance issue: I. Tissue engineering" , Int. J. Biol. Macromol., 25(1-3):111-21 (1999).

(56) References Cited

OTHER PUBLICATIONS

Williams & Peoples, "Biodegradable plastics from plants," CHEMTECH 26:38-44 (1996).
Williams & Peoples, "Making plastics green," Chem. Br. 33:29-32 (1997).
Xie, et al., "Ring-opening polymerization of β-butyrolactone by thermophilic lipases," Macromolecules 30:6997-98 (1997).vbTab.
Zinn, et al., "Occurrence, synthesis and medical application of bacterial polyhydroxyalkanoate", Adv. Drug. Deliv. Rev., 53(1):5-21 (2001).
Poirier, et al., "Progress toward biologically produced biodegradable thermoplastics", Adv. Mater, 5(1):30-7 (1993).
Slater, et al., "Production of poly-(3-hydroxybutyrate-co-3-hydroxyvalerate) in a recombinant *Escherichia coli* strain", Appl Environ Microbiol., 58(4):1089-94 (1992).

FIG. 1

PHA4422

BIOABSORBABLE POLYMER CONTAINING 2-HYDROXYACID MONOMERS

CROSS REFERENCE TO RELATED APPLICATION

This application is a continuation of pending prior application U.S. Ser. No. 10/434,334 filed May 7, 2003, entitled "Bioabsorbable Polymer Containing 2-Hydroxyacid Monomers", by David P. Martin and Frank A. Skraly, which claims benefit of and priority to U.S. Provisional Application Ser. No. 60/379,583 filed on May 10, 2002, both of which are herein incorporated by reference in their entirety.

BACKGROUND OF THE INVENTION

The present invention is generally in the field of methods for making 2-hydroxyacid monomers, and the resulting polyhydroxyalkanoate polymers.

Numerous microorganisms have the ability to accumulate intracellular reserves of poly [(R)-3-hydroxyalkanoates] ("PHA") polymers. PHAs are biodegradable thermoplastic materials, produced from renewable resources, with a broad range of industrial and biomedical applications (Williams and Peoples, 1996, CHEMTECH 26, 38-44). Around 100 different monomers have been incorporated into PHA polymers, as reported in the literature (Steinbüchel and Valentin, 1995, FEMS Microbiol. Lett. 128; 219-228) and the biology and genetics of their metabolism has recently been reviewed (Huisman and Madison, 1998, Microbiology and Molecular Biology Reviews, 63: 21-53).

Fermentation and recovery processes for a range of PHA types have been developed using a variety of bacteria including *Azotobacter, Alcaligenes latus, Comamonas testosteroni* and genetically engineered *E. coli* and *Klebsiella*, as recently reviewed by Braunegg et al., 1998, Journal of Biotechnology 65: 127-161; Choi and Lee, 1999, Appl. Microbiol. Biotechnol. 51: 13-21. More traditional polymer synthesis approaches have also been examined, including direct condensation and ring-opening polymerization of the corresponding lactones (Jesudason and Marchessault, 1994, Macromolecules 27: 2595-2602).

Synthesis of PHA polymers containing the monomer 4-hydroxybutyrate (PHB4HB, Doi, Y. 1995, Macromol. Symp. 98, 585-599) or 4-hydroxyvalerate and 4-hydroxyhexanoate containing PHA polyesters have been described (Valentin et al., 1992, Appl. Microbiol. Biotechnol. 36, 507-514 and Valentin et al., 1994, Appl. Microbiol. Biotechnol. 40, 710-716). The PHB4HB copolymers can be produced with a variety of monomer compositions which provides a range of polymer properties (Saito, Y, Nakamura, S., Hiramitsu, M. and Doi, Y., 1996, Polym. Int. 39: 169). The homopolymer poly(4-hydroxybutyrate), or P4HB, has been synthesized in recombinant *E. coli* (Hein et al., 1997, FEMS Microbiol. Lett. 153: 411-418) by using plasmid-borne *Ralstonia eutropha* PHA synthase (phaC) and the *Clostridium kluyveri* 4HB-CoA transferase (orfZ) genes.

PHA copolymers of 3-hydroxybutyrate-co-3-hydroxypropionate have also been described (Shimamura et. al., 1994, Macromolecules 27: 4429-4435; Cao et. al., 1997, Macromol. Chem. Phys. 198: 3539-3557). The highest level of 3-hydroxypropionate incorporated into these copolymers is 88 mol % (Shimamura et. al., 1994, Macromolecules 27: 4429-4435).

WO 02/08428A2 to Metabolix Inc. describes genetically engineered bacteria for the production of PHA copolymers from polyol feedstocks. Although over 100 different monomers have been incorporated into PHAs in organisms, the presence of glycolic acid in a biosynthetic PHA has never been reported. Glycolic acid is the simplest of the hydroxyacids, and polymers containing glycolic acid previously have been chemically synthesized. For instance, high molecular mass glycolic acid polymers are preferentially prepared by ring opening polymerization from the cyclic dimer, glycolide. Glycolic acid containing polymers are used in absorbable sutures, internal fixations devices, tissue engineering scaffolds, drug release matrices, etc. See, for example, U.S. Pat. No. 3,867,190; U.S. Pat. No. 3,736,646; Fukuzaki, et al., "A new biodegradable copolymer of glycolic acid and lactones with relatively low-molecular weight prepared by direct copolycondensation in the absence of catalysts" in J. Biomed. Mater. Res. 25(3):315-28 (1991). Synthetic polymers containing glycolic acid have been used for absorbable medical devices since the 1970's. See, for example, Chujo, et al., "Ring-opening polymerization of glycolide" in Makromol. Chem. 100:262-6 (1967); Fukuzaki, et al., "Direct copolymerization of glycolic acid with lactones in the absence of catalysts" in Eur. Polym. J. 26(4):457-61 (1990); Kricheldorf, et al., "Polylactones, 2. Copolymerization of glycolide with β-propiolactone, γ-butyrolactone or δ-valerolactone" in Makromol. Chem. 186(5):955-76 (1985); Kricheldorf, et al., "Polylactones, 3. Copolymerization of glycolide with L,L-lactide and other lactones" in Makromol. Chem. 12(Polym. Specific Prop.):955-76 (1985); Nakayama, et al., "Synthesis and biodegradability of novel copolyesters containing γ-butyrolactone units" in Polymer 39(5):1213-1222 (1998); Nakayama, et al., "Syntheses of biodegradable polyesters and effect of chemical structure on biodegradation" in Nippon Kagaku Kaishi 1:1-10 (2001). However, copolymers formed of glycolic acid and various lactones by chemical synthesis have relatively low molecular weights. Moreover, it is difficult to control the stereo configuration of the lactone units in the copolymers formed by chemical synthesis.

It would be useful to be able to incorporate glycolic acid into PHA polymers in bacterial production systems. This would further expand the range of physical properties available from the PHA family of polymers and the presence of the glycolic acid monomers would provide a means for controlling the degradation rate of the PHAs for industrial and biomedical uses. In particular, the incorporation of glycolic acid into PHAs would provide a means of controlling the in vivo degradation rate of PHA biomedical devices using a monomer already having a history of safe use in medical implants.

It is therefore an object of the present invention to provide a method for the biosynthesis of PHAs containing glycolic acid.

It is another object of this invention to provide methods for the biosynthesis of PHAs containing glycolic acid and at least one other monomer such as 3-hydroxybutyric acid, 3-hydroxypropionic acid, 3-hydroxyvaleric acid, 3-hydroxyhexanoic acid, 3-hydroxyoctanoic acid, 3-hydroxydecanoic acid, 4-hydroxybutyric acid or 4-hydroxyvaleric acid. Specific glycolic acid containing PHAs of interest include poly-3-hydroxybutyric acid-co-glycolic acid and poly-glycolic acid-co-4-hydroxybutyric acid.

It is further an object of the present invention to provide PHAs containing 2-hydroxyacids by biosynthesis for medical and industrial applications.

SUMMARY OF THE INVENTION

A class of PHA copolymers containing glycolic acid and method of making and using thereof have been developed. The copolymers containing glycolic acid can be synthesized via biosynthesis by the action of a PHA polymerase in a living cell. By changing the genetic background of the cells one can control specific metabolic pathways that produces the Coenzyme-A thioester of glycolic acid which can be incorporated into PHA polymers by a PHB or PHA synthase enzyme. In a representative embodiment, the method described herein produces glycolic acid containing polymer by expressing in an organism genes encoding polyhydroxyalkanoate synthase (PHA synthase) and enzymes for the formation of glycolyl-CoA. The PHA synthase can be a PHB or PHA synthase. The enzymes for the formation of glycolyl-CoA include, for example, aldehyde dehydrogenase, diol oxidoreductase, and/or acyl-CoA transferase. Additional genes encoding acetoacetyl-CoA reductase, and beta-ketoacyl-CoA thiolase may also be utilized to provide other PHA comonomer precursors such as 3-hydroxybutyryl-CoA. In a preferred embodiment, the resulting PHAs contain glycolic acid and at least one other monomer such as 3-hydroxybutyric acid, 3-hydroxypropionic acid, 3-hydroxyvaleric acid, 3-hydroxyhexanoic acid, 3-hydroxyoctanoic acid, 3-hydroxydecanoic acid, 4-hydroxybutyric acid or 4-hydroxyvaleric acid. Specific glycolic acid containing PHAs of interest include poly-3-hydroxybutyric acid-co-glycolic acid and poly-glycolic acid-co-4-hydroxybutyric acid.

The organism can be a transgenic plant, fungus, yeast, or bacterium. Preferably, the organism is a bacterium. Most preferably, the organism is *E. coli*. In a most preferred embodiment, the *E. coli* have mutations which constituitively express fatty acid oxidation pathways.

The polymers containing glycolic acid monomers can be used to form various medical devices such as for controlled release of therapeutic, prophylactic or diagnostic agents, drug delivery, tissue engineering scaffolds, cell encapsulation; targeted delivery, biocompatible coatings; biocompatible implants; guided tissue regeneration; wound dressings; orthopedic devices; prosthetics and bone cements; or diagnostics.

The PHA polymers containing glycolic acid can be used to form fibers, films, foams or molded articles using standard industrial melt extrusion techniques including melt spinning, melt blown, injection molding, blow molding cast film or blow molding as appropriate. Fibers made from the glycolic acid containing PHAs can be used to make nonwoven or knitted articles useful in clothing, disposable wipes and/or sanitary articles such as diapers or feminine hygiene articles. The polymers containing glycolic acid can be blended with other materials including biodegradable polymers such as polylactic acid, starch or chemically modified starches or synthetic polyesters which contain terepthalic acid, succinic acid, 1,4-butanediol or adipic acid as building blocks and which may be biodegradable. The polymers containing glycolic acid can be formulated with various processing aids including nucleants, plasticizers, crosslinking agents, thermal stabilizers, colorants, fillers and anti-blocking agents.

DETAILED DESCRIPTION OF THE INVENTION

I. Definitions

Figure 1:
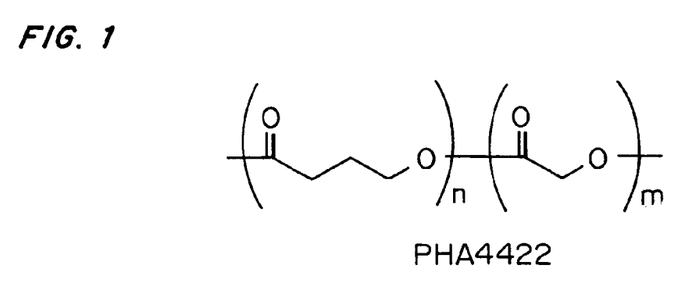
FIG. 1 shows the chemical structure of poly(4-hydroxybutyrate-co-glycolate).

The term P4HB as used here refers to a polyhydroxyalkanoate formed of a monomer having four carbon atoms and a hydroxyl group at the 4-position of the hydroxyacid, which is poly(4-hydroxybutyrate) (P4HB). The term P4HBGA refers to a polyhydroxyalkanoate copolymer formed of a monomer having four carbon atoms and a hydroxyl group at the 4-position of the hydroxyacid, which is 4-hydroxybutyric acid, and a monomer having two carbon atoms and a hydroxyl group at the 2-position of the hydroxyacid, which is glycolic acid. Therefore, the term P4HBGA refers to poly(4-hydroxybutyrate-co-glycolate) (P4HBGA) (FIG. 1).

The term "MG1655/pFS73" as used herein refers to an *E. coli* strain utilizing 4-hydroxybutyric acid (4HB) as a feed to produce 4-hydroxybutyryl-CoA which can be polymerized by a PHB or PHA synthase and is described in WO/0208428 A2.

II. The Poly(hydroxyalkanote-co-Glycolic Acid) Copolymer Compositions (1) Polymer Compositions As used herein, "PHA materials" contain one or more units, for example between 10 and 100,000, and preferably between 100 and 30,000 units, of the following formula I:

—$OCR^1R^2(CR^3R^4)_nCO$—;

and one or more units, for example between 1 and 100,000, and preferably between 10 and 30,000 units, of the following formula II:

—$OCR^1R^2CO$—;

wherein n is an integer, for example between 1 and 15, and in a preferred embodiment, between 1 and 4; and wherein $R^1$, $R^2$, $R^3$, and $R^4$ independently can be hydrogen or hydrocarbon radicals including long chain hydrocarbon radicals; halo- and hydroxy-substituted radicals; hydroxy radicals; halogen radicals; nitrogen-substituted radicals; and/or oxygen-substituted radicals.

As used herein, the formula —$(CR^3R^4)_n$— is defined as including the following formulas:

—$CR^3R^4$— (where $n=1$);

$CR^3R^4CR^{3'}R^{4'}$— (where $n=2$); and

—$CR^3R^4CR^{3'}R^{4'}CR^{3''}R^{4''}$— (where $n=3$);

wherein $R^3$, $R^{3''}$, and $R^{4''}$ can be independently hydrocarbon radicals including long chain hydrocarbon radicals; halo- and hydroxy-substituted radicals; hydroxy radicals; halogen radicals; nitrogen-substituted radicals; oxygen-substituted radicals; and/or hydrogen atoms. Thus, formula I includes units derived from 3-hydroxyacids (n=1), 4-hydroxyacids (n=2), and 5-hydroxyacids (n=3).

The polymers typically have a molecular weight over 300, for example between 300 and $10^8$, and in a preferred embodiment 10,000 to 10,000,000 Daltons.

In a preferred embodiment, the copolymer is a copolymer containing 3-hydroxyacid or 4-hydroxyacid monomers and glycolate monomers. In a specifically preferred embodiment, the copolymer is poly-4-hydroxybutyrate-co-glycolate (P4HBGA).

III. Method for Biosynthesis of PHAs Containing 2-Hydroxyacid Monomer (1) Synthesis of Polyhydroxyalkanoate During the mid-1980's, several research groups were actively identifying and isolating the genes and gene products responsible for PHA synthesis. These efforts led to the development of transgenic systems for production of PHAs in both microorganisms and plants, as well as enzymatic methods for PHA synthesis. Such routes could increase further the available PHA types. These advances have been reviewed in Williams & Peoples, CHEMTECH, 26:38-44 (1996) and Williams & Peoples, Chem. Br. 33:29-32 (1997).

Methods which can be used for producing PHA polymers suitable for subsequent modification to alter their rates of degradation are described, for example, in U.S. Pat. No. 4,910,145 to Holmes, et al.; Byrom, "Miscellaneous Biomaterials" in Biomaterials (Byrom, Ed.), pp. 333-59 (MacMillan Publishers, London 1991); Hocking & Marchessault, "Biopolyesters" in *Chemistry and Technology of Biodegradable Polymers* (Griffin, Ed.), pp. 48-96 (Chapman and Hall, London 1994); Holmes, "Biologically Produced (R)-3-hydroxyalkanoate Polymers and Copolymers," in *Developments in Crystalline Polymers* (Bassett Ed.), vol. 2, pp. 1-65 (Elsevier, London 1988); Lafferty et al., "Microbial Production of Poly-b-hydroxybutyric acid" in *Biotechnology* (Rehm & Reed, Eds.) vol. 66, pp. 135-76 (Verlagsgesellschaft, Weinheim 1988); Müller & Seebach, *Angew. Chem. Int. Ed. Engl.* 32:477-502 (1993); Steinbüchel, "Polyhydroxyalkanoic Acids" in *Biomaterials* (Byrom, Ed.), pp. 123-213 (MacMillan Publishers, London 1991); Williams & Peoples, CHEMTECH, 26:38-44, (1996); Steinbüchel & Wiese, *Appl. Microbiol. Biotechnol.*, 37:691-697 (1992); U.S. Pat. Nos. 5,245,023; 5,250,430; 5,480,794; 5,512,669; and 5,534,432; Agostini, et al., *Polym. Sci.*, Part A-1, 9:2775-87 (1971); Gross, et al., *Macromolecules*, 21:2657-68 (1988); Dubois, et al., *Macromolecules*, 26:4407-12 (1993); Le Borgne & Spassky, *Polymer*, 30:2312-19 (1989); Tanahashi & Doi, *Macromolecules*, 24:5732-33 (1991); Hori, et al., *Macromolecules*, 26:4388-90 (1993); Kemnitzer, et al., *Macromolecules*, 26:1221-29 (1993); Hori, et al., *Macromolecules*, 26:5533-34 (1993); Hocking, et al., *Polym. Bull.*, 30:163-70 (1993); Xie, et al., *Macromolecules*, 30:6997-98 (1997); U.S. Pat. No. 5,563,239 to Hubbs; U.S. Pat. Nos. 5,489,470 and 5,520,116 to Noda, et al. The PHAs derived from these methods may be in any form, including a latex or solid form.

Identification, cloning and expression of the genes involved in the biosynthesis of PHAs from several microorganisms within recombinant organisms allow for the production of PHAs within organisms that are not native PHA producers. A preferred example is *E. coli*, which is a well recognized host for production of biopharmaceuticals, and PHAs for medical applications. Such recombinant organisms provide researchers with a greater degree of control of the PHA production process because they are free of background enzyme activities for the biosynthesis of unwanted PHA precursors or degradation of the PHA. Additionally, the proper selection of a recombinant organism may facilitate purification of, or allow for increased biocompatibility of, the produced PHA.

The minimal requirements for the synthesis of PHA in a recombinant organism are a source of hydroxyalkanoyl-CoA and an appropriate PHA synthase (Gerngross & Martin, *Proc. Natl. Acad. Sci.* 92:6279-83 (1995)). Recombinant PHA producers thus require a biosynthetic pathway for a hydroxyalkanoyl-CoA monomer and a suitable PHA synthase. Production of a homopolymer requires that the organism produce only one suitable substrate for the PHA synthase, as production of multiple substrates results in the formation of a PHA copolymer. For example, recombinant organisms containing a transgene encoding a PHA synthase are sufficient for production of P4HB.

Figure 2:
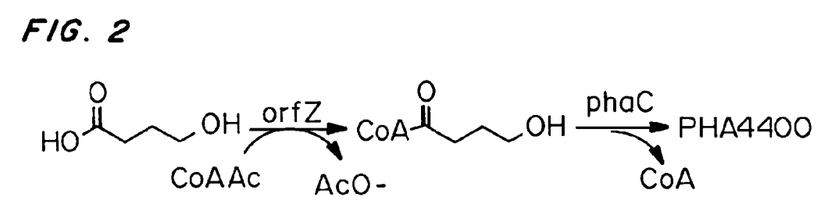
FIG. 2 is the pathway for producing poly(4-hydroxybutyrate) in MG1655/pFS73.
Figure 3:
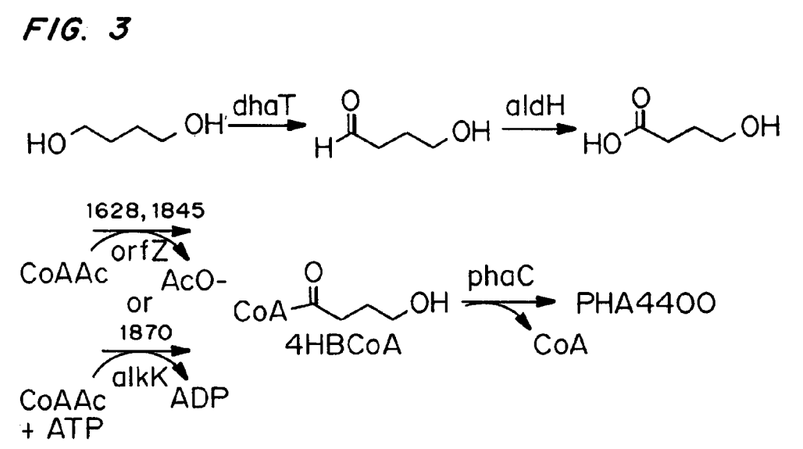
FIG. 3 illustrates the pathway for producing poly(4-hydroxybutyrate) from 1,4-butanediol.
Figure 4:
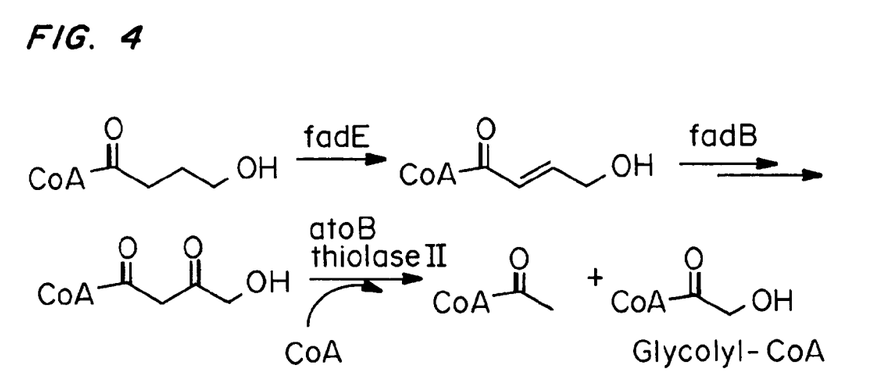
FIG. 4 illustrates the pathway for oxidation of 4-hydroxybutyryl-CoA via the fad and ato systems.
Figure 5:
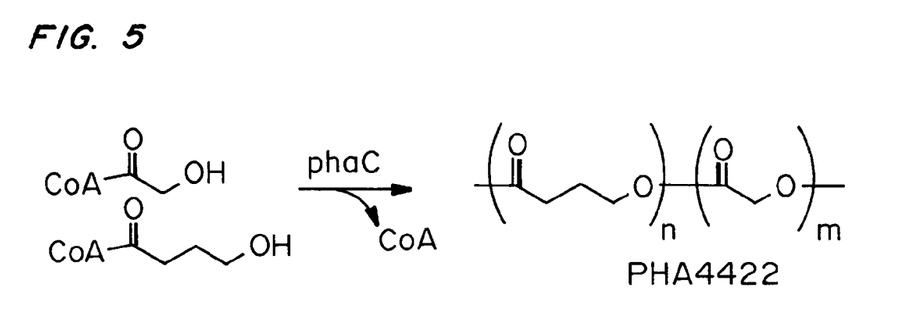
FIG. 5 shows the pathway for production of poly(4-hydroxybutyrate-co-glycolate).

In one embodiment, the pathway leading to the production of poly-4-hydroxybutyrate (P4HB) in the genetically engineered *E. coli* strain MG1655/pFS73 utilizing 4-hydroxybutyric acid (4HB) as a feed is described in WO/0208428 A2 (FIG. 2). When 4HB is used as a feed, P4HB is accumulated in the cells by a pathway involving activation of the 4HB to 4HB-CoA by a transesterification reaction with acetyl-CoA catalyzed by an acyl-CoA transferase encoded by the gene orfZ and subsequent polymerization of 4HB-CoA by PHA synthase (phaC) (FIG. 2). As FIG. 3 shows, this pathway can be modified to allow production of P4HB from 1,4-butanediol. This modified pathway involves the products of two additional genes (dhaT and aldH) to oxidize the 1,4-butanediol in situ to 4HB. Formation of P4HB proceeds as in MG1655 through orfZ and phaC.

(2) Synthesis of PHAs Containing 2-Hydroxyacid Monomer

The pathways leading to the synthesis of PHAs can be modified to incorporate glycolate to form copolymers containing 2-hydroxyacid units. For example, under certain fermentation conditions, genetically engineered *E. coli* strains previously constructed for the production of P4HB and poly (3-hydroxybutyrate-co-4-hydroxybutyrate) (PHB4HB) (WO 0208428A2) can produce a new PHA composition, poly-4-hydroxybutyrate-co-glycolate (P4HBGA) (FIG. 1).

The incorporation of of glycolic acid monomers can be achieved by co-expressing, for example, a PHA synthase and enzymes leading to the formation of glycolyl-CoA in an organism such as *E. coli*. Additionally, by controlling the genetic background of the organism strains, one can control the cells' ability to incorporate glycolate units into the PHA. Therefore, by changing the genetic background of the cells, one can control specific metabolic pathways for control of the level of glycolate co-monomer in the PHA polymer.

Pathways leading to the production of PHAs containing glycolic acid monomers can be expressed in an organism such as yeast, bacteria, fungi, and plants, preferably bacteria, most preferably *E. coli*. For example, *E. coli* production strains can be engineered on the basis of a parent strain with additional gene or genes to incorporate glycolic acid monomers. The pathways can also be constructed to generate Glycolyl-CoA, in situ. For example, Glycolyl-CoA, the glycolate monomer in the biosynthesis of PHAs containing glycolate units, can be formed via co-expressing enzymes that catalyze butanediol oxidation. Other pathways for the production of PHAs can be constructed to incorporate genes by expressing enzymes, e.g., acyl transferases, that catalyze the formation of glycolyl-CoA via external feeding, e.g., glycolic acid feeding.

The methodology described can be used to biosynthesize copolymers having 2-hydroxyacid units and other hydroxyacid units such as 3-hydroxyacid by expressing genes encoding, for example, PHA synthases, and genes leading to the formation of 3-hydroxyacyl-CoA, and 2-hydroxyacyl-CoA such as butanediol oxidization genes (dhaT and aldH).

In addition to using biological routes for the synthesis of PHA copolymers containing 2-hydroxyacid units, PHA copolymers may also be derived by chemical synthesis. One widely used approach involves the ring-opening polymerization of lactone monomers with or without various catalysts or initiators (see, for example, Chujo, et al., "Ring-opening polymerization of glycolide" in Makromol. Chem. 100:262-6 (1967); Fukuzaki, et al., "Direct copolymerization of glycolic acid with lactones in the absence of catalysts" in Eur. Polym. J. 26(4):457-61 (1990); Kricheldorf, et al., "Polylactones, 2. Copolymerization of glycolide with β-propiolactone, γ-butyrolactone or δ-valerolactone" in Makromol. Chem. 186(5): 955-76 (1985); Kricheldorf, et al., "Polylactones, 3. Copolymerization of glycolide with L,L-lactide and other lactones" in Makromol. Chem. 12 (Polym. Specific Prop.):955-76 (1985); Nakayama, et al., "Synthesis and biodegradability of novel copolyesters containing γ-butyrolactone units" in Polymer 39(5):1213-1222 (1998); Nakayama, et al., "Syntheses of biodegradable polyesters and effect of chemical structure on biodegradation" in Nippon Kagaku Kaishi 1:1-10 (2001)). A second approach involves condensation polymerization of esters and is described in U.S. Pat. No. 5,563,239 to Hubbs, et al. Researchers also have developed chemo-enzymatic methods to prepare PHAs. For example, Xie et al., *Macromolecules*, 30:6997-98 (1997) disclose a ring-opening polymerization of beta-butyrolactone by thermophilic lipases to yield PHB.

IV. PHA Copolymer Compositions and the Use Thereof as Medical Devices

The polymers described herein can form various polymer compositions, which are useful for preparing a variety of biodegradable medical devices.

Devices prepared from the PHA copolymers described herein can be used for a wide range of different medical applications. Examples of such applications include controlled release of therapeutic, prophylactic or diagnostic agents; drug delivery; tissue engineering scaffolds; cell encapsulation; targeted delivery; biocompatible coatings; biocompatible implants; guided tissue regeneration; wound dressings; orthopedic devices; prosthetics and bone cements (including adhesives and/or structural fillers); and diagnostics.

The PHA copolymers described herein can be used to encapsulate, be mixed with, or be ionically or covalently coupled to any of a variety of therapeutic, prophylactic or diagnostic agents. A wide variety of biologically active materials can be encapsulated or incorporated, either for delivery to a site by the polyhydroxyalkanoate, or to impart properties to the polymer, such as bioadhesion, cell attachment, enhancement of cell growth, inhibition of bacterial growth, and prevention of clot formation.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. The polymer can also be used to encapsulate cells and tissues. Representative diagnostic agents are agents detectable by x-ray, fluorescence, magnetic resonance imaging, radioactivity, ultrasound, computer tomography (CT) and positron emission tomography (PET). Ultrasound diagnostic agents are typically a gas such as air, oxygen or perfluorocarbons.

In the case of controlled release, a wide range of different bioactive compounds can be incorporated into a controlled release device. These include hydrophobic, hydrophilic, and high molecular weight macromolecules such as proteins. The bioactive compound can be incorporated into the PHAs in a percent loading of between 0.1% and 70% by weight, more preferably between 5% and 50% by weight. The PHAs may be in almost any physical form, such as a powder, film, molded item, particles, spheres, latexes, and crystalline or amorphous materials. They can be combined with additional non-PHA materials, for example, other polymers. They are suitable for use in applications requiring slowly degrading, biocompatible, moldable materials, for example, medical devices. Examples of medical devices which can be prepared from the polymers include rods, bone screws, pins, surgical sutures, stents, tissue engineering devices, drug delivery devices, wound dressings, and patches such as hernial patches and pericardial patches.

Degradable implants fabricated with the PHA copolymers described herein may be used in a wide range of orthopedic and vascular applications, tissue engineering, guided tissue regeneration, and applications currently served by other thermoplastic elastomers (McMillin, *Rubber Chem. Technol.*, 67:417-46 (1994)). The implants may include other factors to stimulate repair and healing. Preferred devices are tubes suitable for passage of bodily fluids. These devices may be modified with cell attachment factors, growth factors, peptides, and antibodies and their fragments.

Preferred methods of fabricating medical devices include solvent casting, melt processing, extrusion, injection and compression molding, and spray drying. Particles are preferably prepared directly from a fermentation based process, or by a solvent evaporation technique, double emulsion technique, or by microfluidization, using methods available in the art. (Koosha, F. Ph.D. Dissertation, 1989, Univ. Nottingham, UK., *Diss. Abstr. Int. B* 51:1206 (1990); Bruhn, B. W. and Müeller, B. W. *Proceed. Intern. Symp. Control. Rel. Bioact. Mater.* 18:668-69 (1991); Conti, B. et al., *J. Microencapsulation*, 9:153-166 (1992); Ogawa, Y. et al., *Chem. Pharm. Bull.*, 36:1095-103 (1988); Mathiowitz, E. and Langer, R. "Polyanhydride microspheres as drug delivery systems," M. Donbrow Ed., in "*Microcapsules Nanopart. Med. Pharm.*" CRC, Boca Raton, Fla., 1992, Ch. 5, pp. 99-123.)

The PHA copolymers described herein can be fabricated into devices suitable for wound healing. For example, non-woven fibrous materials for this purpose may be prepared from the polymers by first producing polymer fibers, by pressing the polymers through a perforated outlet, using procedures known to those skilled in the art. The fibers can then be fabricated into a porous membrane (cloth) by spreading them on a solid support and subjecting them to compression molding. The thickness of the device is preferably less than 500 μm. The wound healing device may also be prepared by perforating a film or membrane using a laser to achieve porosity, or using a leaching technique to prepare a porous material. The pore sizes should ideally be small enough to lock out cells and other tissue matter. The wound healing devices may be positioned in vivo to separate tissues and stimulate tissue regeneration.

The PHA copolymers described herein may be used to encapsulate cells. Using procedures known to those skilled in the art, cells first may be pre-coated. Maysinger, *Reviews in the Neurosciences*, 6:15-33 (1995). Using a particle encapsulation procedure such as the double emulsion technique, the cells may then be encapsulated by PHAs. Ogawa, et al., *Chem. Pharm. Bull.*, 36:1095-103 (1988). Encapsulated cells may then be implanted in vivo.

The PHA copolymers described herein may be fabricated into tissue engineering scaffolds using a wide range of polymer processing techniques. Preferred methods of fabricating PHA tissue engineering scaffolds include solvent casting, melt processing, fiber processing/spinning/weaving, extrusion, injection and compression molding, lamination, and solvent leaching/solvent casting. Such methods are known to those skilled in the art.

One preferred method of fabricating a PHA copolymers described herein tissue engineering scaffold involves using an extruder, such as a Brabender extruder. For example, this technique can be used to prepare extruded tubes suitable for implantation in a range of lengths and sizes.

Another preferred method involves preparing a nonwoven PHA scaffold from fibers. Fibers may be produced from the melt or solution, and processed into nonwovens using methods known to those skilled in the art. The properties of the nonwoven may be tailored by varying, for example, the PHA material, the fiber dimensions, fiber density, material thickness, fiber orientation, and method of fiber processing. The porous membranes may, if desired, be further processed. For example, these membranes may be formed into hollow tubes.

Another preferred method involves melt or solvent processing a suitable PHA into an appropriate mold and perforating the material using a laser or other means to achieve the desired porosity. Also preferred are methods that include rolling a compression molded PHA sheet into a loop and heat sealing. The PHA sheet optionally may be rolled with another material, such as a second biodegradable polymer. For example, the latter material could be a nonwoven of polyglycolic acid, polylactic acid, or a copolymer of glycolic and lactic acids. Such a procedure should provide a laminated tube suitable for use in the engineering of new vessels, ducts and tubes. The PHAs may also be used to coat other tissue engineering scaffolds. Such materials could be derived from other degradable polymers. Coating may be performed, for example, with a solvent based solution, or by melt techniques, or using a PHA latex.

The tissue engineering devices described herein may be seeded with cells prior to implantation or after implantation. The cells may be harvested from a healthy section of the donor's tissue, expanded in vitro using cell culture techniques, and then seeded into a scaffold (or matrix) either prior to or after implantation. Alternatively, the cells may be obtained from other donor's tissue or from existing cell lines.

The PHA copolymers described herein may be used to coat other devices and materials. Such coatings may improve their properties for medical application, for example, improving their biocompatibility and mechanical properties, and tailoring their degradation and controlled release profiles. The PHA copolymers described herein may be coated onto other devices using the fabrication procedures described above. The thickness of the coating can be adjusted to the needs of the specific application by changing the coating weight or concentration applied, and/or by overcoating.

The PHA copolymers described herein may be fabricated into stents using a wide range of polymer processing techniques. Preferred methods of fabricating PHA stents include solvent casting, melt processing, fiber processing/spinning, extrusion, injection molding, and compression molding. Such methods are known to those skilled in the art.

Prior to implantation, a bioresorbable polymeric article must be sterilized to prevent disease and infection of the recipient. Sterilization is performed prior to seeding a polymeric device with cells. Heat sterilization of PHA containing articles is often impractical since the heat treatment could deform the article, especially if the PHA has a melting temperature below that required for the heat sterilization treatment. This problem can be overcome using cold ethylene oxide gas as a sterilizing agent. Exposure of a PHA containing article to vapors of ethylene oxide prior to implantation sterilizes the article making it suitable for implantation. During sterilization with cold ethylene oxide gas, the PHA containing article maintains its shape. This type of treatment is ideally suited for sterilization of molded, or pre-formed articles where the shape of the article plays in important role in its proper functioning.

The devices described herein can be administered systemically or locally, or even used in vitro, particularly for cell culture. The preferred methods of systemically administering the devices are by injection, inhalation, oral administration and implantation. Other suitable methods for administering the devices include administering the devices topically, as a lotion, ointment, patch, or dressing.

The PHA polymers described herein are broadly useful as replacements for traditional petrochemical polymers in a range of applications with particular utility where biodegradability or production from renewable resources is advantageous.

The following examples further illustrate the methods disclosed herein and the copolymers formed thereby.

EXAMPLES

Example 1

Production of P4HB in MBX1928

Description of the Strains MBX1628 and MBX1928

MBX1928 is based on the wild-type *Escherichia coli* strain MG1655 (CGSC#6300) and expresses four inserted genes: aldH (aldehyde dehydrogenase) from *E. coli*, dhaT (diol oxidoreductase) from *Klebsiella pneumoniae* (Johnson and Lin, 1987, *J. Bacteril.* 169:2050-2054), orfZ (acyl-CoA transferase) from *Clostridium kluyveri* (Söhling and Gottschalk, 1996, *J. Bacteriol.* 178:871-880), and phaC (PHA synthase) from *Ralstonia eutropha*. The aldH and dhaT genes are inserted into the chromosome (along with the tetracycline resistance marker gene from transposon Tn10), and the orfZ and phaC genes are present on a plasmid, along with the kanamycin resistance marker from the plasmid pACYC177.

MBX1628 has the same inserted genes as MBX1928, except that it is based on the *Escherichia coli* strain LS5218 (CGSC#6966). LS5218 and MG1655 are closely related with the notable exception that LS5218 contains two mutations, fadR601 and atoCcon. As a result of these mutations, the fadR repressor gene for the fad system is not active, and the fad system is not repressed, while the inducer for the ato system (atoC) is constitutively expressed, so that the ato system is constitutive.

MBX1870 is identical to MBX1628, except that it expresses the *Pseudomonas oleovorans* alkK (acyl-CoA transferase) gene (van Bellen et al., 1992, *Mol. Microbiol.* 6:3121-3136) in place of the *Clostridium kluyveri* orfZ gene.

The strains described above are summarized in Table 1. The inserted genes allow these strains to produce PHAs when fed an appropriate feedstock, such as 1,4-butanediol.

TABLE 1

Description of E. coli strains used.

| Strain | Parent Strain | Relevant genotype | Inserted genes |
|---|---|---|---|
| MBX1628 | LS5218 | fadR601, atoC(con) | aldH, dhaT, orfZ, phaC |
| MBX1870 | LS5218 | fadR601, atoC(con) | aldH, dhaT, alkK, phaC |
| MBX1928 | MG1655 | fadR+ atoC+ | aldH, dhaT, orfZ, phaC |

The cloning and isolation of various genes necessary for the construction of the gene constructs disclosed herein are well documented (see, for example, Skraly et al., *Appl. Environ. Microbiol.* 64:98-105 (1998); Söhling and Gottschalk, *J. Bacteriol.* 178:871-880 (1996); Sambrook et al., Molecular cloning: A Laboratory Manual, $2^{nd}$ ed., Cold Spring Harbor Laboratory Press, Cold Spring Harbor, N.Y., 1989). The construction of the various gene constructs described herein is also well within the knowledge in the art (Herrero et al., *J. Bacteriol.* 172:6557-67 (1990)). Techniques of conjugation of the aldH, dhaT, and tetA genes into the bacterial, i.e., *E. coli*, chromosome and transformation are described in, for example, Herrero et al., ibid; Miller, Experiments in Molecular Genetics, Cold Spring Harbor Laboratory Press, Cold Spring Harbor, N.Y., 1972; Sambrook et al., supra.

Identification of P4HB2GA

Various analytical tests confirm the presence of glycolic acid in the polymer. After extraction of the polymer from the biomass and purification by selective precipitation, the polymer was analyzed by nuclear magnetic resonance (NMR). In the NMR spectrum, the presence of the glycolic acid comonomer is indicated by a singlet peak at 4.6 ppm and two additional triplets at 4.2 and 2.5 ppm with suspected peaks under the multiplet at 1.9 ppm. The singlet peak comes from glycolic acid while the additional peaks arise from different diads of 4HB-GA and GA-4HB.

Polymer samples with a high comonomer content were available from low-feed-rate experiments with strain MBX1870. These samples were helpful for identifying the comonomer peak by GC. The glycolic acid peak has a relatively short retention time of about 4.0 minutes and a peak shape similar to other hydroxyacid butyl ester derivatives. Glycolide standards and spiking of copolymer sample confirmed this peak as butyl glycolate.

General Description of GC Butanolysis

Dry PHA biomass (5-20 mg) was digested at 110° C. for 2 hours in 3 mL of butanolysis reagent (9 parts butanol, 1 part concentrated hydrochloric acid, containing 2 mg/ml diphenylmethane). After cooling to room temperature, the mixture was washed with 3 mL of water, and the upper, organic layer was removed for GC analysis. GC analysis was performed on an HP6890 GC equipped with an SPB-1 column and a FID detector. GC conditions were as follows: 80° C. 2 minutes, 10° C./min to 250° C., 250° C. 2 minutes; carrier gas, helium, 2 mL/min; approximate splitting ratio 1:50; injection volume 1 µl. Quantitative determinations were made by comparisons of peak areas versus the standards gamma-butyrolactone and glycolide (the cyclic dimer of glycolic acid), for the 4-hydroxybutyric and glycolic acids respectively.

General Description of GPC Analysis

Polymer samples were extracted from the dry biomass (0.5 g) into chloroform (10 mL) for at least 2 hours. The resultant solution was filtered through a paper filter and the polymer was precipitated by addition of the chloroform solution to methanol (50 mL). The precipitated polymer was collected and allowed to air dry. A chloroform solution of the polymer (1 mg/mL) was analyzed at room temperature by GPC using a flow rate of 1 mL/minute over a PLGel 5 µm mixed column from Polymer Labs (Amherst, Mass.). Weight-average molecular weight was calculated relative to polystyrene standards of narrow polydispersity.

Fermentation Processes

Fermentation inocula were grown in 200 mL sterile LB medium (10 g/L tryptone, 5 g/L yeast extract, 5 g/L NaCl) supplemented with 50 mg/L kanamycin sulfate and 15 mg/L tetracycline hydrochloride. Each inoculum was incubated at 30° C. in a rotary shaker agitated at approximately 200 rpm for 16 to 18 hours, then used to inoculate a 2- or 5-L fermentor. The initial fermentor medium contained, per liter: glucose, 5 g; yeast extract, 20 g; soy peptone, 20 g; $Na(NH_4)HPO_4$, 3.5 g; $K_2HPO_4.3H_2O$, 7.5 g; $KH_2PO_4$, 3.7 g; $MgSO_4$, 0.602 g; $FeSO_4.7H_2O$, 5.56 mg; $CoSO_4.7H_2O$, 5.62 mg; $ZnSO_4.7H_2O$, 0.58 mg; $MnCl_2.4H_2O$, 3.96 mg; $CaCl_2.2H_2O$, 3.34 mg; $CuCl_2.2H_2O$, 0.34 mg; thiamine hydrochloride, 10 mg; MAZU DF-204 or Breox FMT-30 antifoam, 0.2 mL; kanamycin sulfate, 50 mg; tetracycline hydrochloride, 15 mg. The glucose and 1,4-butanediol feed solutions were each at a concentration of 500 g/L.

Fermentation Conditions

The fermentation was run at 30° C. The pH was controlled to 7.0 (±0.2) by addition of dilute $NH_4OH$ (15%) or dilute sulfuric acid (3%). The air flow was set to a constant flow rate (1 vvm). The dissolved oxygen was controlled to 25% saturation by varying stirrer speed. On-line measurements of pH, temperature, dissolved oxygen concentration and agitation (rpm) were made through continuous data acquisition. Glucose concentration and $OD_{600}$ were measured off-line.

After inoculation of the fermentor, the cells were grown to an $OD_{600}$ of 50 (approximately 4-5 hours). The production of PHA was initiated by the batch addition of 1,4-butanediol at 1 to 5 g/L (depending upon desired feed rate of 1,4-butanediol). Thereafter the fermentor was supplemented with the glucose and 1,4-butanediol feeds. The 1,4-butanediol feed rate was maintained at 1 to 5 g/L/hr. The glucose feed was maintained at approximately 5 g/L/hr. Glucose concentration was measured off-line initially every hour and feed rate was adjusted to keep the glucose concentration <1 g/L (preferably near 0.1 g/L). Fermentation was run for approximately 48 hours total. Cells were collected by centrifugation at 5,000 g for 10 minutes and washed with water. Cell pellets were dried by lyophilization for later extraction of the polymer into chloroform and analysis. The polymer composition and concentration in the biomass were analyzed by GC butanolysis. The molecular weight of the PHA was determined by GPC analysis of the purified polymer samples. Results for the different strains at different feed rates are shown in Table 2 below.

TABLE 2

Composition, yield and molecular-weight analysis of PHA produced in engineered E. coli at various feed rates of 1,4-butanediol.

| Strain | 1,4-butanediol feed rate (g/L-h) | Glycolate in PHA (wt. %) | Yield PHA (g/L) | $M_w$ of PHA (g/mol) |
|---|---|---|---|---|
| MBX1628* | 5 | 3 | 57 | 581,000 |
| MBX1628* | 3 | 2 | 71 | 330,000 |
| MBX1870 | 3 | 0 | 18 | N.D.** |
| MBX1870 | 2 | 2 | 25 | N.D.** |
| MBX1870 | 1 | 12 | 15 | N.D.** |
| MBX1928 | 5 | 0 | 31 | 455,000 |
| MBX1928* | 3 | 0 | 66 | 529,000 |
| MBX1928 | 2 | 0 | 42 | 669,000 |

*Data values are averages from two separate experiments.
**N.D. = Not determined.

The strains with constitutive pathways of fatty acid degradation (MBX1628 and MBX1870) incorporated glycolic acid into the polymer product when fed 1,4-butanediol, while the strain with wild-type (and hence uninduced) pathways of fatty acid degradation (MBX1928) did not incorporate glycolic acid under the same conditions.

Those skilled in the art will recognize, or be able to ascertain using no more than routine experimentation, many equivalents to the specific embodiments of the methods and compositions described herein. Such equivalents are intended to be encompassed by the following claims.

We claim:

1. A method of producing a glycolic acid-containing polyhydroxyalkanoate polymer comprising
   Providing a feedstock comprising glycolic acid, 1,4-butanediol, 4-hydroxybutyric acid, or combinations thereof to bacteria expressing a polyhydroxyalkanoate (PHA) synthase and at least one enzyme selected from the group consisting of acetoacetyl-CoA reductases and beta-ketoacyl-CoA thiolases and at least one enzyme for the production of glycolyl-CoA selected from the group consisting of aldehyde dehydrogenase, diol oxidoreductase, enoyl-CoA dehydrase, beta acyl-CoA dehydrogenase, thiolases, and acyl-CoA transferase,
   to produce the glycolic acid-containing polyhydroxyalkanoate polymer.

2. The method of claim 1 wherein the PHA synthase is a synthase of poly(3-hydroxyalkanoate) or poly(4-hydroxyalkanaote).

3. The method of claim 1 wherein the PHA synthase is poly(3-hydroxyalkanoate) synthase.

4. The method of claim 1 wherein the PHA synthase is poly(4-hydroxyalkanoate) synthase.

5. The method of claim 4 wherein the PHA synthase is poly(4-hydroxybutyrate) synthase.

6. The method of claim 1 wherein the bacteria is *E. coli*.

7. The method of claim 1 wherein the bacteria is *E. coli* having mutations selected from fadR601 and atoC constitutive mutations.

8. The method of claim 1 wherein the aldehyde dehydrogenase is from *E. coli*, wherein the diol oxidoreductase is from *Klebsiella pneumoniae*, and wherein the acyl-CoA transferase is from *Clostridium kluyveri*.

9. The method of claim 1 comprising feeding 1,4-butanediol and glucose to the bacteria.

10. The method of claim 1 comprising feeding glycolic acid to the bacteria.

11. The method of claim 1 comprising feeding 4-hydroxybutyric acid to the bacteria.

* * * * *

UNITED STATES PATENT AND TRADEMARK OFFICE
CERTIFICATE OF CORRECTION

| | |
|---|---|
| PATENT NO. | : 8,703,449 B2 |
| APPLICATION NO. | : 13/250492 |
| DATED | : April 22, 2014 |
| INVENTOR(S) | : David P. Martin and Frank A. Skraly |

It is certified that error appears in the above-identified patent and that said Letters Patent is hereby corrected as shown below:

In the Claims

Claim 1, column 13, line 13, replace "Providing" with --providing--.
Claim 1, column 13, lines 13-14, replace "1,4-butanedial" with --1,4-butanediol--.

Signed and Sealed this
Twenty-sixth Day of May, 2015

Michelle K. Lee
*Director of the United States Patent and Trademark Office*

UNITED STATES PATENT AND TRADEMARK OFFICE
CERTIFICATE OF CORRECTION

PATENT NO. : 8,703,449 B2
APPLICATION NO. : 13/250492
DATED : April 22, 2014
INVENTOR(S) : David P. Martin and Frank A. Skraly Page 1 of 1

It is certified that error appears in the above-identified patent and that said Letters Patent is hereby corrected as shown below:

Title page item (73), Assignee, please insert --Tepha, Inc., Lexington, MA (US)-- after "Metabolix, Inc., Cambridge, MA (US)".

Signed and Sealed this
Fifth Day of April, 2016

Michelle K. Lee
*Director of the United States Patent and Trademark Office*